United States Patent [19]
Vince et al.

[11] Patent Number: 4,916,224
[45] Date of Patent: Apr. 10, 1990

[54] DIDEOXYCARBOCYCLIC NUCLEOSIDES

[75] Inventors: Robert Vince, St. Paul; Mei Hua, Minneapolis, both of Minn.

[73] Assignee: Regents of the University of Minnesota, Minneapolis, Minn.

[21] Appl. No.: 146,252

[22] Filed: Jan. 20, 1988

[51] Int. Cl.$^4$ .................. C07D 473/02; C07D 473/26; C07D 473/40; A61K 31/52

[52] U.S. Cl. .................................... 544/254; 544/264; 544/265; 544/267; 544/276; 544/277

[58] Field of Search ............... 544/254, 276, 277, 265, 544/267, 264; 514/261, 262, 258

[56] References Cited

U.S. PATENT DOCUMENTS

| | | | |
|---|---|---|---|
| 3,817,982 | 6/1974 | Verheyden et al. | 530/26 |
| 3,917,837 | 11/1975 | Lin et al. | 514/261 |
| 4,076,711 | 2/1978 | Ganguly et al. | 544/254 |
| 4,138,562 | 2/1979 | Vince | 544/326 |
| 4,383,114 | 5/1983 | Vince | 544/277 |
| 4,543,255 | 9/1985 | Shealy et al. | 514/258 |
| 4,742,064 | 5/1988 | Vince | 514/258 |

FOREIGN PATENT DOCUMENTS

| | | | |
|---|---|---|---|
| 236935 | 9/1987 | European Pat. Off. | |
| 0219284 | 12/1984 | Japan | 544/277 |

OTHER PUBLICATIONS

Santi et al., Chemical Abstracts, vol. 76:22492h (1972).
Thomas et al., Chemical Abstracts, vol. 68:49934a (1968).
Santi et al., Chemical Abstracts, vol. 78:132248g (1973).
Coward et al., Chemical Abstracts, vol. 79:87815x (1973).
S. Broder, ed., *AIDS-Modern Concepts and Therapeutic Challenges*, Marcel Dekker, Inc., NY (1987), p. 320.
J. P. Horwitz et al., *J. Org. Chem.*, 32, 817 (1967).
J. Balzarini et al., *Biochem. Biophys. Res. Comm.*, 140, 735 (1986).
T.-S. Lin et al., *Biochem. Pharmacol.*, 36, 311 (1987).
T.-S. Lin et al., *J. Med. Chem.*, 30, 440 (1987).
P. Herdewijn et al., *J. Med. Chem.*, 30, 1270 (1987).
J. Balzarini et al., *Molec. Pharmacol.*, 32, 162 (1987).
M. Baba et al., *Biochem. Biophys. Res. Commun.*, 142, 128 (1987).
H. Lee and R. Vince, *J. Pharm. Sci.*, 69, 1019 (1980).
R. Vince et al., *J. Med. Chem.*, 27, 1358 (1984).
R. Vince et al., *J. Med. Chem.*, 20, 612 (1977).
L. B. Townsend, in Nucleoside Analogues–Chemistry, Biology and Medical Applications, R. T. Walker, E. DeClerq and F. Eckstein, eds., Plenum Press, NY (1979), pp. 193–223.
R. Vince et al., *Science*, 221, 1405 (1983).
Shealy et al., *J. Pharm. Sci.*, 62, 1432 (1973).
H. J. Schaeffer et al., *J. Pharm. Sci.*, 53, 1510 (1964).
Y. F. Shealy et al., *J. Heterocycl. Chem.*, 10, 601 (1973).

*Primary Examiner*—Mukund J. Shah
*Assistant Examiner*—Diana G. Rivers
*Attorney, Agent, or Firm*—Merchant, Gould, Smith, Edell, Welter & Schmidt

[57] ABSTRACT

Antiviral and antitumor compounds are disclosed of general formula:

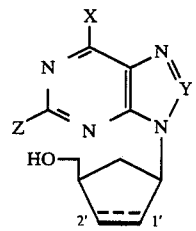

wherein Z is H, OH or $NH_2$, Y is CH or N, the bond indicated by $C_1'$--$C_2'$ is absent or, in combination with the $C_1'$--$C_2'$ bond is the unit CH=CH, and X is selected from the group consisting of H, $N(R_2)$, SR, OR or halogen, wherein R is H, lower ($C_1$–$C_4$)alkyl, aryl or mixtures thereof, and the pharmaceutically acceptable salts thereof.

14 Claims, 1 Drawing Sheet

3b, Z = H, Z' = NH$_2$
4b, Z = NH$_2$, Z' = H
5b, Z = NH$_2$, Z' = -N=N-Ar-pCl
6b, Z = NH$_2$, Z' = NH$_2$

DIDEOXYCARBOCYCLIC NUCLEOSIDES

GRANT INFORMATION

This invention was made with Government support under Grant No. 5 R 01 CA23263, awarded by the National Institutes of Health. The Government has certain rights in this invention.

FIELD OF THE INVENTION

The present invention relates to dideoxycarbocyclic nucleosides which exhibit antiviral and cytotoxic activity.

BACKGROUND OF THE INVENTION

Despite intensive effort to discover drugs that may be of value in the systemic treatment of human immunodeficiency virus (HIV) infections, such infections have been singularly resistant to chemotherapy. The intracellular and intimate relation to nuclear metabolism of virus reproduction makes it difficult to destroy a virus without irreparable damage to the host cell.

The discovery of the antiviral activity of vidarabine (9-β-D-arabinofuranosyladenine monohydrate) has led to the preparation of a large number of synthetic nucleosides. To date, only one synthetic nucleoside, 3'-azido-3'-deoxythymidine has been approved for treating certain AIDS patients, but it is a palliative, not a cure.

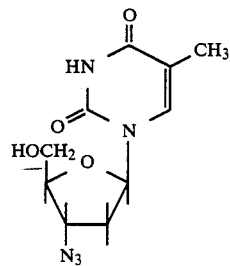

(AZT)

Although AZT is specifically active against retroviruses, its use has lead to side effects, including anemia, headache, confusion, anxiety, nausea and insomnia. The nucleoside analog, 2'-3'-dideoxycyfide (DDC), exhibits an in vitro $TI_{50}$ of ca. 300 against HIV and may exhibit fewer side effects than AZT, but may also be eliminated more rapidly from the body.

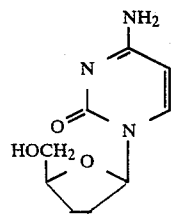

(DDC)

The synthesis of adenine ("6-amino-purine") nucleoside analogs in which the pentose sugar has been replaced with tris(hydroxy)-substituted cyclopentyl residues has yielded compounds with substantial cytotoxic and antiviral activity. For example, the carbocyclic analog of vidarabine, cyclaridine, is highly active against HSV-2, but exhibits a low therapeutic index ($TI_{50}=10$) against HIV in vitro. Likewise, the carbocyclic analog of AZT is inactive against HIV. Therefore, it is clear that the structure-activity relationships between the variously substituted carbocyclic nucleosides which have been prepared and tested remain ill-defined.

Thus, a substantial need exists for chemotherapeutic agents effective to protect mammalian cells against infection by viruses such as HSV-2, HIV, varicella-zoster, vaccinia, human cytomegalovirus (HCMV) and the like.

SUMMARY OF THE INVENTION

The present invention is directed to hydroxymethyl-cyclopentyl or -cyclopentenyl-substituted purines and 8-aza-purines of the formula (I):

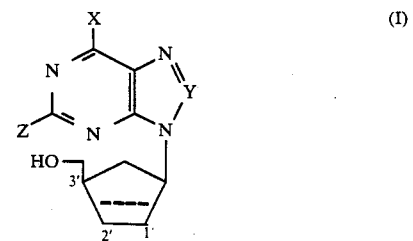

(I)

wherein Z is H, OH or $NH_2$, Y is CH or N, the bond indicated by—is either absent or, in combination with the $C_1'-C_2'$ bond, is the unit CH=CH and X is selected from the group consisting of H, $N(R)_2$, SR, OR and halogen, wherein R is H, lower($C_1-C_4$)alkyl, aryl or mixtures thereof, and the pharmaceutically acceptable salts thereof. Preferably, X is Cl, OH or $NH_2$, Y is CH, R is phenyl or H, and the bond indicated by—is present. Certain of these compounds are effective antiviral and/or cytotoxic agents or are intermediates useful for the preparation thereof.

Although generally, compounds of formula I are not active against HSV-1, it is expected that some of them will exhibit specific antiviral activity against other viruses such as HSV-2, HCMV and/or HIV. Specifically, the compound of formula I, wherein X is OH, Z is $NH_2$, Y is CH and the bond—is present, (14a) strongly inhibits HIV infectivity in vitro. The $TI_{50}$ of this compound varied with the infected cell line which was used to assay for anti-HIV activity, but generally fell between 200–400, and was determined to be as high as 667 in one assay. Compound 14a is also active against HSV-1. Compounds of formula I wherein X is Cl or $NH_2$, Y is CH, Z is $NH_2$ and the bond—is present (13a and 15a, respectively) are also active against HIV. Compounds of the formula I wherein Y=N, Z=$NH_2$, X=Cl or OH and the bond indicated by—is either absent or present, are cytotoxic to cultured P-388 leukemia cells.

It is believed that the antiviral activity is due to an inhibitory effect on the ability of viruses to infect normal mammalian cells. The present invention is also directed to the intermediate compound of the formula (II):

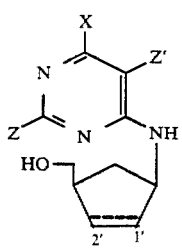

(II)

wherein Z is H or NH$_2$, Z' is H or NH$_2$, X is halogen, preferably Cl, and the bond indicated by—is either absent or, in combination, with C$_1$'–C$_2$' bond, is the unit CH═CH, which is useful for the preparation of the purines of the invention. Preferably, Z is NH$_2$, and Z' is H or both Z and Z' are NH$_2$. However, the compounds where X═Cl, Z═NH$_2$ and Z'═H or NH$_2$ are not active against HIV.

The (3-hydroxymethylcyclopentenyl)pyrimidine analog, 20a, is also within the scope of the present invention. Its synthesis from cyclopentene 2a is outlined in Scheme I, below.

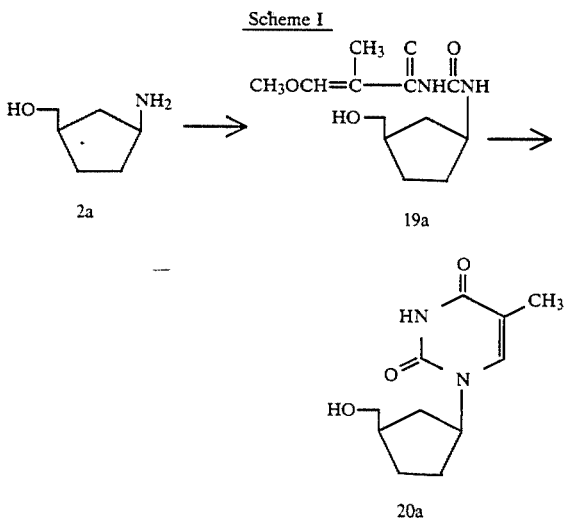

Thus, it is expected that certain of the compounds of the present invention will be useful against viral infections or virus-associated tumors, and the method of their use to inhibit viral infectivity or tumor growth in vitro or in vivo is also within the scope of the present invention. More specifically, the 2',3'-dideoxyadenosine compounds of formula I, wherein Z is H, X is Cl, OH, NH$_2$ or SH, Y is CH and the C$_1$'–C$_2$' bond is absent have been previously reported by H. J. Schaeffer et al., J. Pharm. Sci., 53, 1510 (1964), and been disclosed to be not useful against HIV. See AIDS-Modern Concepts and Therapeutic Challenges, S. Broder, ed., M. Dekker, Inc., New York, N.Y., (1987) at pages 316–317. Likewise, compound I, wherein Z is H, X is NH$_2$, Y is N and the C$_1$'–C$_2$' bond is absent has been reported by Y. F. Shealy et al., J. Heterocycl. Chem., 10, 601 (1973), but has not been disclosed to be active against HIV.

DETAILED DESCRIPTION OF THE INVENTION

Figure 1:
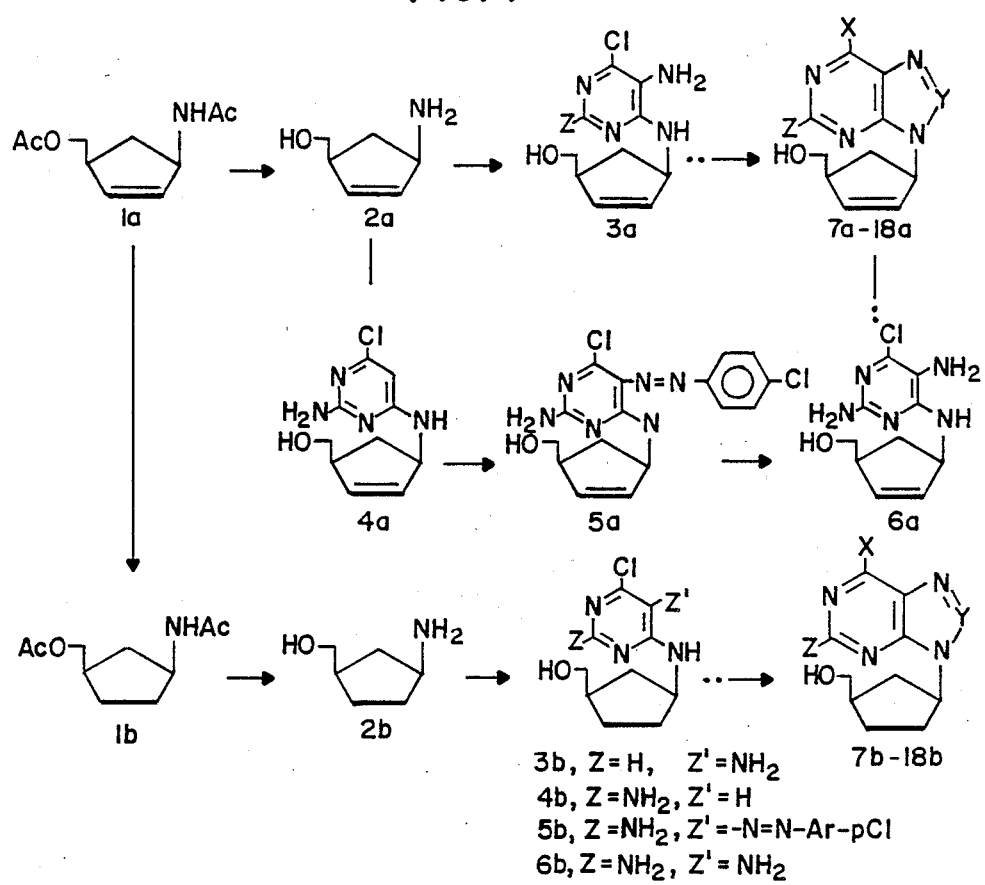
FIG. 1 is a flow diagram summarizing the synthesis of the purines of the present invention.

FIG. 1 outlines the synthesis of preferred compounds of formulas I and II from starting materials 1a and 1b. The structural formulas and some of the properties of compounds 7a–18a and 7b–18b are summarized on Table I, below.

TABLE I

| A. 2',3'-Dideoxy-6-Substituted-Purines of Formula I, Z = H. | | | | | | |
|---|---|---|---|---|---|---|
| Compound No. | X | Y | (C$_1$'–C$_2$')* | M.P. (°C.) | Rf | Yield (%) |
| 7a | Cl | CH | + | 108–110 | 0.35[a] | 82 |
| 7b | Cl | CH | − | 120–122 | 0.33[a] | 86 |
| 8a | OH | CH | + | 248–250(dec) | 0.24[b] | 45 |
| 8b | OH | CH | − | 276–278(dec) | 0.23[b] | 60 |
| 9a | NH$_2$ | CH | + | 198–200 | 0.33[b] | 81 |
| 9b | NH$_2$ | CH | − | 146–148 | 0.30[b] | 77 |
| 10a | SH | CH | + | 263–265(dec) | 0.44[b] | 73 |
| 10b | SH | CH | − | 297–300(dec) | 0.42[b] | 69 |
| 11a | OH | N | + | 180–182 | 0.38[b] | 49 |
| 11b | OH | N | − | 179–182 | 0.37[b] | 69 |
| 12a | NH$_2$ | N | + | 220–222(dec) | 0.45[b] | 69 |
| 12b | NH$_2$ | N | − | 195–196 | 0.44[b] | 79 |
| B. 2'-3'-Dideoxy-2,6-Disubstituted-Purines of Formula I, Z = NH$_2$. | | | | | | |
| Compound No. | X | Y | (C$_1$'–C$_2$')* | M.P. (°C.) | Rf[b] | Yield (%) |
| 13a | Cl | CH | + | 145–147 | 0.64 | 80 |
| 13b | Cl | CH | − | 151–153 | 0.62 | 73 |
| 14a | OH | CH | + | 254–256(dec) | 0.27 | 61 |
| 14b | OH | CH | − | 274–276(dec) | 0.25 | 77 |
| 15a | NH$_2$ | CH | + | 152–155 | 0.41 | 80 |
| 15b | NH$_2$ | CH | − | 208–211 | 0.39 | 77 |
| 16a | Cl | N | + | 153–155(dec) | 0.69 | 81 |
| 16b | Cl | N | − | 170–172(dec) | 0.67 | 82 |
| 17a | OH | N | + | 223–225(dec) | 0.40 | 89 |
| 17b | OH | N | − | 228–231 | 0.38 | 81 |
| 18a | NH$_2$ | N | + | 240–242(dec) | 0.52 | 83 |
| 18b | NH$_2$ | N | − | 223–225 | 0.50 | 88 |

*+ = present (cyclopentenyl ring);
− = absent (cyclopentyl ring).
[a] CHCl$_3$:MeOH, 10:1.
[b] CHCl$_3$:MeOH, 5:1.

Compounds 7a, 7b, 8b, 9a, 9b, 10a, 10b, 13a, 14a, 14b, 15a, and 15b, are effective in the anti-HIV assay described in Example 36. Likewise, compounds 3a, 3b, 4a, 4b, 5a, 5b, 6a, 6b, 19a and 20a, shown on FIG. 1, are effective to inhibit the infection and killing of human T lymphocytes (T$_h$ cells) by HIV. Therefore, these compounds are candidates for clinical trials in human patients infected with HIV and/or afflicted with AIDS or AIDS-related complex (ARC).

DETAILED DESCRIPTION OF THE INVENTION

The synthesis of the hydroxymethylcyclopentenyl compounds of formula 7a–18a and the hydroxymethylcyclopentyl compounds of formulas 7b–18b, from the versatile precursor, 1α-acetylamino-3α-acetoxymethyl-cyclopent-2-ene (1a) was accomplished as outlined in FIG. 1. Compound 1a was prepared as described in U.S. Pat. No. 4,138,562, the disclosure of which is incorporated by reference herein. Compound 2a was prepared from compound 1a by hydrolysis in the presence of a mild base, such as an alkaline earth metal hydroxide. To afford the pyrimidine compound 3a, compound 2a was reacted with an excess of 5-amino-4,6-dichloropyrimidine in the presence of an amine base, such as a trialkylamine, in an alcoholic solvent. Likewise, the cyclopentanyl compound 1b, which is obtained from compound 1a by hydrogenation, is hydrolyzed and reacted with 5-amino-4,6-dichloropyrimidine to yield the pyrimidinylcyclopentyl carbinol, 3b. Also, 2-amino-4,6-dichloropyrimidine was reacted with compound 2a to yield compound 4a, and with compound 2b to yield compound 4b.

Para-chloroaniline was diazotized with acidic sodium nitrite and reacted with compound 4a and 4b to yield the chlorophenylazo intermediates 5a and 5b, respectively. Reduction of the azo intermediates 5a and 5b to yield 6a and 6b, respectively, was accomplished with zinc and acetic acid. See Shealy and Clayton, *J. Pharm. Sci.*, 62, 1433 (1973).

The 5-amino-6-chloro-4-pyrimidinyl intermediates 3a and 3b were converted to the 9-substituted-6-chloropurines 7a and 7b, respectively, by ring closure with triethylorthoformate and subsequent mild acid hydrolysis to remove ethoxymethylidenes and formates formed during the reaction. In like manner, the 2,5-diamino-6-chloro-4-pyrimidinyl intermediates 6a and 6b were ring-closed to the corresponding 2-amino-6-chloro-9H-purin-9-yl compounds 13a and 13b.

The 6-chloropurines 7a, 7b, 13a and 13b were converted to the corresponding 6-hydroxy purines 8a, 8b, 14a and 14b, respectively, with aqueous base, i.e., by refluxing them with an alkali metal hydroxide such as NaOH. Chloro compounds 7a, 7b, 13a, 13b, 16a and 16b were converted to the corresponding amino compounds 9a, 9b, 15a, 15b, 18a and 18b, by reaction with liquid ammonia under pressure.

Mono- or disubstituted 6-amino compounds of formula I, wherein X is NR$_2$ and R=R=(lower)alkyl, phenyl or mixtures thereof with H can be prepared by conventional methods for the conversion of halides to secondary or tertiary amines. For example, see I. T. Harrison et al., *Compendium of Organic Synthetic Methods*, Wiley-Interscience, N.Y. (1971) at pages 250-252. The 6-chloro substitutent in compounds 7a, 7b, 13a, 13b, 16a and 16b can be replaced with other halogen atoms by the use of various p-(halo)benzene diazonium chlorides in the conversion of 4a to 5a or of 4b to 5b, or by conventional methods of halide-halide exchange.

These conversions are extensively described in the context of purine nucleoside synthesis in *Nucleoside Analogs-Chemistry, Biology and Medical Applications*, R. T. Walker et al., eds., Plenum Press, N.Y. (1979) at pages 193-223, the disclosure of which is incorporated by reference herein.

Treatment of 7a and 7b with thiourea in refluxing alcohol, followed by alkaline hydrolysis afforded thiols 10a and 10b, respectively. See L. F. Fieser et al., *Reagents for Organic Synthesis*, John Wiley and Sons, Inc., N.Y. (1967) at pages 1165-1167 and U.S. Pat. No. 4,383,114, the disclosures of which are incorporated by reference herein. Phenyl or alkylthioderivates can be prepared from the corresponding thiols by the procedure of U.S. Pat. No. 4,383,114 (Example 6).

Ring closure of 3a and 3b with acidic aqueous sodium nitrate followed by neutralization with aqueous base directly afforded the corresponding 7-hydroxy-3H-1,2,3-triazolo[4,5d]pyrimidin-3-yl compounds 11a and 11b, respectively. Ring closure of 6a and 6b afforded the corresponding 5-amino-7-chloro-3H-1,2,3-triazo[4,5-d]pyrimidin-3-yl compounds 16a and 16b, respectively, which were hydrolyzed to the corresponding 7-hydroxy compounds 17a and 17b with aqueous NaOH. Compound 3a was converted to the corresponding 7-amino compounds 12a by reaction with acidic sodium nitrite, followed by reaction of the crude product with liquid ammonia. The 7-aminocyclopentyl carbinol 12b was prepared by hydrogenating 12a (Pd-C). Compounds of formula I, wherein Z is OH, X is NH$_2$ or OH, and Y is CH can be prepared from compounds 14a, 14b, 15a or 15b by deamination of the 2-amino group with nitrous acid, employing the procedure used by Davoll to convert 2-aminoadenosine to isoguanosine. See J. Davoll, *J. Amer. Chem. Soc.*, 73, 3174 (1951), the disclosure of which is incorporated by reference herein.

Compounds of formula I, wherein X is H, Z is NH$_2$ and Y is CH can be prepared from compounds 7a, 7b, 13a or 13b by dehalogenation with zinc/water [J. R. Marshall et al., *J. Chem. Soc.*, 1004 (1951)] or by photolysis in dry nitrogen-purged tetrahydrofuran containing 10% triethylamine in a Rayonet photochemical reactor (2537Å) by the method of V. Nair et al., *J. Org. Chem.*, 52, 1344 (1987).

Pharmaceutically acceptable acid salts of compounds 7-18 can be prepared as described in U.S. Pat. No. 4,383,114, the disclosure of which is incorporated by reference herein.

The invention will be further described by reference to the following detailed examples wherein elemental analyses were performed by M-H-W Laboratories, Phoenix, AZ. Melting points were determined on a Mel-Temp apparatus and are corrected. Nuclear magnetic resonance spectra were obtained on Jeol FX 90QFT or Nicollet NT300 spectrometers and were recorded in DMSO-D$_6$. Chemical shifts are expressed in ppm downfield from Me$_4$Si. IR spectra were determined as KBr pellets with a Nicollet 50XC FT-IR spectrometer, and UV spectra were determined on a Beckmann DU-8 spectrophotometer. Mass spectra were obtained with an AEI Scientific Apparatus Limited MS-30 mass spectrometer. Thin layer chromatography (TLC) was performed on 0.25 mm layers of Merck silica gel 60F-254 and column chromatography on Merck 60 silica gel (230-400 mesh). All chemicals and solvents are reagent grade unless otherwise specified.

EXAMPLE 1

($\pm$)-(1$\alpha$,4$\alpha$)-4-[(5-Amino-6-chloro-4-pyrimidinyl)-amino]-2-cyclopentenylcarbinol (3a)

A mixture of 1a (3.0 g, 15 mmol) and aqueous barium hydroxide (0.5N, 300 ml) was refluxed overnight. After cooling, it was neutralized with dry ice. The precipitate was filtered out, and the aqueous solution was concentrated to dryness. The residue was extracted with absolute ethanol and concentrated again to yield 2a as a colorless syrup 1.6 g (14 mmol).

To this syrup, 5-amino-4,6-dichloropyrimidine (4.59 g, 28 mmol), triethylamine (4.2 g, 42 mmol), and n-butanol (50 ml) were added and the mixture was refluxed for 24 hr. The volatile solvents were removed, the residue was absorbed on silica gel (7 g), packed in a flash column (4.0×12 cm) and eluted with CHCl$_3$-MeOH (20:1) to yield 2.69 g (74%) of compound 3a; mp 130°-132° C. An analytical sample was obtained by recrystalization from ethyl acetate (EtOAc), mp 134°-135° C., MS (30 ev, 200° C.); m/e 240 and 242 (M$^+$ and M$^+$+2), 209 (M$^+$-31), 144 (B$^+$); IR:

3600–2600 (OH), 1620,1580 (C=C, C=N); Anal. (C$_{10}$H$_{13}$ClN$_4$O) C,H,N.

EXAMPLE 2

(±)-(1α,3α)-3[(5-Amino-6-chloro-4-pyrimidinyl)-amino]cyclopentylcarbinol (3b)

Starting material 1a (2 g, 10 mmol) was dissolved in ethanol (30 ml) and hydrogenated in the presence of 10% palladium-charcoal (20 mg). The catalyst was filtered out and solvent was evaporated. The residual syrup (1b) was hydrolyzed by a barium hydroxide solution as described in Example 1, hereinabove.

To the resultant syrup (2b, (10 mmol)), 5-amino-4,6-dichloropyrimidine (20 mmol), triethylamine (30 mmol) and n-butanol (35 ml) were added and the mixture was refluxed for 24 hr. The reaction mixture was processed as described above for the synthesis of 3a from 2a to yield 1.62 g (67%) of 3b, mp 161°–163° C. Further recrystalization from ethyl acetate yielded a material of mp 163°–165° C. MS (30 ev, 200° C.): m/e 242 and 244 (M+ and M++2), 211 (M+-31), 144 (B+):IR: 3600–2600 (OH), 1620, 1580 (C=C,C=N); Anal. (C$_{10}$H$_{15}$ClN$_4$O), C,H,N.

EXAMPLE 3

(±)-(1α,4α)-4-[(2-Amino-6-chloro-4-pyrimidinyl)-amino]-2-cyclopentenylcarbinol (4a)

To 14 mmol of crude 2a, 2-amino-4,6-dichloropyrimidine (3.74 g, 22.8 mmol), triethylamine (15 ml) and n-butanol (75 ml) were added and the mixture was refluxed for 48 hr. The volatile solvents were removed, residue was treated with methanol to separate the undissolved by-product (the double pyrimidine nucleoside). The methanol solution was absorbed on silica gel (8 g) packed into a column (4.0×14 cm) and eluted with CHCl$_3$-MeOH (40:1) to yield 1.52 g (42%) of crude 4a. The product was recrystalized from ethyl acetate to yield 4a; mp 132°–134° C., MS (30 ev, 200° C.); m/e 240 and 242 (M+ and M++2), 209 (M+-31), 144 (B+); IR: 3600–3000 (NH$_2$, OH), 1620,1580 (C=C, C=N); Anal. (C$_{10}$H$_{13}$ClN$_4$O) C,H,N.

EXAMPLE 4

(±)-(1α,3α)-3-[(2-Amino-6-chloro-4-pyrimidinyl)-amino]cyclopentylcarbinol (4b)

To 2b (25 mmol), 2-amino-4,6-dichloropyrimidine (37.5 mmol), triethylamine (25 ml) and n-butanol (125 ml) were added and the mixture was refluxed for 48 hr. It was processed as described in Example 4a to yield 2.7 g (44%) of crystaline 4b, mp 122°–124° C. Recrystalization from ethyl acetate yielded 4b of mp 124°–126° C. MS (30 ev, 200° C.); m/e 242 and 244 (M+ and M++2), 211 (M+-31), 144 (B+); IR: 3600–3000 (NH$_2$, OH), 1620,1580 (C=C, C=N); Anal. (C$_{10}$H$_{15}$ClN$_4$O) C,H,N.

EXAMPLE 5

(±)-(1α,4α)-4-{[(2-Amino-6-chloro-5-(4-chlorophenyl)azo]-4-pyrimidinyl-amino}-2-cyclopentenylcarbinol (5a)

A cold diazonium salt solution was prepared from p-chloroaniline (1.47 g, 11.5 mmol) in 3N HCl (25 ml) and sodium nitrite (870 mg, 12.5 mmol) in water (10 ml). This solution was added to a mixture of 4a (2.40 g, 10 mmol), acetic acid (50 ml), water (50 ml) and sodium acetate trihydrate (20 g). The reaction mixture was stirred overnight at room temperature. The yellow precipitate was filtered and washed with cold water until neutral, then it was air-dried in the fumehood to yield 3.60 g (94%), of 5a, mp 229° C. (dec). The analytical sample was obtained from acetone-methanol (1:2), mp 241°–243° C. (dec). MS (30 ev, 260° C.): m/e 378 and 380 (M+ and M++2), 282 (B+); IR: 3600–3000 (NH$_2$, OH), 1620,1580 (C=C, C=N); Anal. (C$_{16}$H$_{16}$Cl$_2$N$_6$O) C,H,N.

EXAMPLE 6

(±)-(1α,3α)-3-{[(2-Amino-6-chloro-5-(4-chlorophenyl)azo]-4-pyrimidinyl-amino}-cyclopentylcarbinol (5b).

A cold diazonium salt solution prepared as described in Example 5 was added to a mixture of 4b (2.42 g, 10 mmol), acetic acid (50 ml) water (50 ml) and sodium acetate trihydrate (20 g). Following the procedures of Example 5, compound 5b was obtained as a yellow product, 3.69 g (94%), mp 260°–262° C. (dec). The crude product was recrystalized from acetone-methanol (3:1), MS (30 ev, 260° C.); m/e 380 and 382 (M+ and M++2), 282 (B+); IR: 3600–3000 (NH$_2$, OH), 1620,1580 (C=C, C=N); Anal. (C$_{16}$H$_{18}$Cl$_2$N$_6$O) C,H,N.

EXAMPLE 7

(±)-(1α,4α)-4-[(2,5-Diamino-6-chloro-4-pyrimidinyl-amino]-2-cyclopentenylcarbinol (6a).

A mixture of 5a (379 mg, 1 mmol), zinc dust (0.65 g, 10 mmol), acetic acid (0.32 ml), water (15 ml) and ethanol (15 ml) was refluxed under nitrogen for 3 hr. The zinc was removed and the solvents were evaporated. The residue was absorbed on silica gel (2 g), packed into a column (2.0×18 cm), and eluted with CHCl$_3$-MeOH (15:1). A pink syrup was obtained. Further purification from methanol-ether yielded 6a as pink crystals, 170 mg (66%), mp 168°–170° C., MS (30 ev, 220° C.); m/e 255 and 257 (M+ and M++2), 224 (M+-31), 159 (B+); IR: 3600–3000 (NH$_2$, OH), 1620,1580 (C=C, C=N); Anal. (C$_{10}$H$_{14}$ClN$_5$O) C,H,N.

EXAMPLE 8

(±)-(1α,3α)-3-[(2,5-Diamino-6-chloro-4-pyrimidinyl)amino]-cyclopentylcarbinol (6b)

A mixture of 5b (3.08 g, 8.1 mmol), zinc dust (5.2 g, 80 mmol), acetic acid (2.6 ml), water (130 ml) and ethanol (130 ml) was refluxed under nitrogen for 3 hr, and worked up as described in Example 7, above. The mixture was absorbed on silica gel (18 g), packed in a column (4.0×8 cm) and eluted with CHCl$_3$-MeOH (20:1) to yield 6b as yellow-pink crystals, 1.44 g (69%). The product was recrystalized from methanolether to yield 6b, mp 143°–145° C., MS (30 ev, 200° C.); m/e 257 and 259 (M+ and M++2), 226 (M+-31), 159 (B+); IR: 3600–3000 (NH$_2$, OH), 1620,1580 (C=C, C=N); Anal. (C$_{10}$H$_{16}$ClN$_5$O) C,H,N.

EXAMPLE 9

(±)-(1α,4α)-4-(6-chloro-9H-purin-9-yl)-2-cyclopentenylcarbinol (7a)

A mixture of 3a (1.30 g, 5.4 mmol), triethyl orthoformate (30 ml) and hydrochloric acid (12N, 0.50 ml) was stirred overnight at room temperature. The solvent was evaporated at 35° C. in vacuo. To the residue was added aqueous hydrochloric acid (0.5N, 30 ml) and the mixture was stirred for 1 hr. The mixture was neutralized to pH 7–8 with 1N sodium hydroxide and absorbed onto silica gel (8 g), packed in a column (4.0×8 cm), and eluted with CHCl$_3$-MeOH (20:1) to yield white crystals of 7a, 1.12 g (82%). The crude product was recrystalized from ethyl acetate to yield 7a, mp 108°–110° C., MS (30 ev, 200° C.); m/e 250 and 252 (M+ and M++2), 219 (M+-31), 154 (B+); IR; 3600–2800 (OH), 1600 (C=C, C=N); Anal. (C$_{11}$H$_{11}$ClN$_4$O) C,H,N.

EXAMPLE 10

(±)-(1α,3α)-3-(6-Chloro-9H-purin-9-yl)-cyclopentyl-carbinol (7b)

A mixture of 3b (1.29 g, 5.3 mmol), triethyl orthoformate (30 ml) and hydrochloric acid (12N, 0.50 ml) was stirred overnight at room temperature and processed as described in Example 9 to yield white crystals of 7b, 1.15 g (86%). The crude product was recrystalized from ethyl acetate to yield 7b, mp 120°–122° C., MS (30 ev, 180° C.); m/e 252 and 254 (M+ and M++2), 221 (M+-31), 154 (B+); IR; 3600–2800 (OH), 1600 (C=C, C=N); Anal. (C$_{11}$H$_{13}$ClN$_4$O) C,H,N.

EXAMPLE 11

(±)-(1α,4α)-4-(6-Hydroxy-9H-purin-9-yl)-2-cyclopentenyl-carbinol (8a)

A mixture of 7a (251 mg, 1 mmol) and aqueous sodium hydroxide (0.2N, 10 ml) was refluxed for 3 hr. After cooling, the reaction mixture was adjusted to pH 5–6 with acetic acid. The reaction mixture was absorbed on silica gel (2 g) packed in a column (2.0×11 cm) and eluted with CHCl$_3$-MeOH (10:1) to yield 105 mg (45%) of 8a. The crude white product was recrystalized from water-methanol (3:1) to yield 8a, mp 248°–250° C. (dec), MS (30 ev, 300° C.); m/e 232 (M+), 214 (M+-18), 136 (B+); IR; 3600–2600 (OH), 1680,1600 (C=O, C=C, C=N); Anal. (C$_{11}$H$_{12}$N$_4$O$_2$) C,H,N.

EXAMPLE 12

(±)-(1α,3α)-3-(6-Hydroxy-9H-purin-9-yl)-cyclopentyl-carbinol (8b)

A mixture of 7b (378 mg, 1.5 mmol) and aqueous sodium hydroxide (0.2N, 15 ml) was refluxed for 3 hr. The mixture was processed as described in Example 11 to yield 213 mg (60%) of 8b, mp 276°–278° C. (dec), MS (30 ev, 280° C.); m/e 234 (M+), 216 (M+-18), 136 (B+); IR: 3600–2600 (OH), 1680,1600 (C=O, C=C, C=N); Anal. (C$_{11}$H$_{14}$N$_4$O$_2$) C,H,N.

EXAMPLE 13

(±)-(1α,4α)-4-(6-Amino-9H-purin-9-yl)-2-cyclopentenylcarbinol (9a)

Liquid ammonia was passed into a bomb containing a solution of 7a (250 mg, 1 mmol) in methanol (5 ml) at −80° C. The bomb was sealed and heated at 60° C. for 24 hr. Ammonia and methanol were evaporated and the residue was recrystalized from water to yield off-white crystals of 9a, 187 mg (81%), mp 198°–200° C. MS (30 ev, 210° C.): m/e 231 (M+), 213 (M+-18), 135 (B+); IR: 3600–2600 (NH$_2$, OH), 1700,1600 (C=C, C=N); Anal. (C$_{11}$H$_{13}$N$_5$O) C,H,N.

EXAMPLE 14

(±)-(1α,3α)-3-(6-Amino-9H-purin-9-yl)-cyclopentyl-carbinol (9b).

Compound 7b (252 mg, 1 mmol) was reacted with ammonia and processed as described in Example 13. The residue was absorbed on silica gel (0.8 g) packed in a column (1.0×10 cm) and eluted with CHCl$_3$-MeOH (10:1). The resultant product was recrystalized from methanolethyl acetate to yield white crystals of 9b, 179 mg (77%), mp 146°–148° C. MS (70 ev, 200° C.): m/e 233 (M+), 216 (M+-17), 135 (B+); IR: 3600–2600 (NH$_2$, OH), 1700,1600 (C=C, C=N); Anal. (C$_{11}$H$_{15}$N$_5$O) C,H,N.

EXAMPLE 15

(±)-(1α,4α)-4-(6-Mercapto-9H-purin-9-yl)-2-cyclopentenyl-carbinol (10a)

A mixture of 7a (125 mg, 0.5 mmol), thiourea (40 mg, 0.64 mmol) and n-propanol (5 ml) was refluxed for 2 hr. After cooling, the precipitate was isolated by filtration, washed with n-propanol, and dissolved in sodium hydroxide (1N, 5 ml). The solution was adjusted to pH 5 with acetic acid. The crude 10a (90 mg, 73%) was isolated again, mp 260°–262° C. (dec) and was recrystalized from N,N-dimethylformamide, to yield 10a, mp 263°–265° C. (dec). MS (30 ev, 290° C.): m/e 248 (M+), 230 (M+-18), 152 (B+); IR: 3600–3200 (OH), 3100,2400 (SH), 1600 (C=C, C=N); Anal. (C$_{11}$H$_{12}$N$_4$OS) C,H,N.

EXAMPLE 16

(±)-(1α,3α)-3-(6-Mercapto-9H-purin-9-yl)-cyclopentylcarbinol (10b)

A mixture of 7b (252 mg, 1 mmol), thiourea (95 ml, 1.25 mmol) and n-propanol (12 ml) was refluxed for 2 hr. The reaction mixture was processed as described in Example 15 to yield a crude product which was recrystalized from methanol to yield white crystals of 10b, 173 mg (69%), mp 297°–300° C. (dec). MS (30 ev, 280° C.): m/e 250 (M+), 233 (M+-17), 152 (B+); IR: 3600–3200 (OH), 3100,2400 (SH), 1600 (C=C, C=N); Anal. (C$_{11}$H$_{14}$N$_4$OS) C,H,N.

EXAMPLE 17

(±)-(1α,4α)-4-(7-Hydroxy-3H-1,2,3-triazolo[4,5-d]pyrimidin-3-yl)-2-cyclopentenyl carbinol (11a).

To a cold solution of 3a (361 mg, 1.5 mmol) in hydrochloric acid (1N, 30 ml) was added sodium nitrite solution (120 mg, 1.7 mmol) in 3 ml of water. The reaction was monitored by starch-potassium iodide paper. The mixture was concentrated at 40° C. to a volume of 2 ml and adjusted to pH 7 with aqueous sodium hydroxide. The mixture was absorbed on silica gel (2 g), packed in a column (2.0×13 cm) and eluted with CHCl$_3$-MeOH (10:1). The crude 11a was recrystallized from water-methanol (3:1) to yield white crystals of 11a, 173 mg (49%) mp 180°–182° C. MS (30 ev, 230° C.): m/e 233 (M+), 203 (M+-30), 137 (B+); IR: 3600–2600 (OH), 1740,1600 (C=O, C=C, C=N); Anal. (C$_{10}$H$_{11}$N$_5$O$_2$) C,H,N.

EXAMPLE 18

(±)-(1α,3α)-3-(7-Hydroxy-3H-1,2,3-triazolo[4,5-d]pyrimidin-3-yl)-cyclopentyl carbinol (11b)

Compound 3b (363 mg, 1.5 mmol) was processed as described in Example 17 and recrystallized from water-methanol to yield 242 mg (269%) of 11b, mp 179°–182° C. MS (30 ev, 280° C.): m/e 235 (M+), 204 (M+-31), 137 (B+); IR: 3600–2600 (OH), 1740,1600 (C=O, C=C, C=N); Anal. (C$_{10}$H$_{13}$N$_5$O$_2$) C,H,N.

EXAMPLE 19

(±)-(1α,4α)-4-(7-Amino-3H-1,23,-triazolo[4,5-d]pyrimidin-3-yl)-2-cyclopentenyl carbinol (12a)

Sodium nitrite solution (828 mg, 12 mmol) in water (10 ml) was added dropwise to a cold solution of 3a (2.43 g, 10.1 mmol) in hydrochloric acid (0.5N, 40 ml). The reaction mixture was stirred at room temperature for 1 hr, then concentrated to a syrup. The syrup was dissolved in ethanol and transferred into a strainless steel bomb. Liquid ammonia was passed in, the bomb was sealed, and the reaction mixture was stirred at room temperature overnight. Ammonia was evaporated and the residue was chromatographed on silica gel (150 g) eluting with $CH_2CL_2$-MeOH (10:1) to yield white crystals of 12a, 1.62 g (69%), mp 220°-222° C. (dec). MS (30 ev, 220° C.): m/e 232 (M+), 202 (M+-30), 136 (B+); IR: 3600-2800 ($NH_2$, OH), 1700,1600 (C=C, C=N); Anal. ($C_{10}H_{12}N_6O$) C,H,N.

EXAMPLE 20

(±)-(1α,3α)-3-(7-Amino-3H-1,2,3-triazolo[4,5-d]pyrimidin-3-yl)-cyclopentyl carbinol (12b)

Compound 12a (200 mg, 0.86 mmol) was dissolved in ethanol (25 ml) and hydrogenated in the presence of 10% palladium-charcoal (30 mg) under 49 lbs/in² of $H_2$ for 18 hrs. The catalyst was removed and the solvent was evaporated. The resultant crude product was recrystallized from ethanol-water (1:2) to yield white crystals of 12b, 173 mg (86%), mp 195°-196° C. MS (70 ev, 190° C.): m/e 234 (M+), 203 (M+-31), 136 (B+); IR: 3600-2800 ($NH_2$, OH), 1700,1600 (C=C, C=N); Anal. ($C_{10}H_{14}N_6O$) C,H,N.

EXAMPLE 21

(±)-(1α,4α)-4-(2-Amino-6-chloro-9H-purin-9-yl)-2-cyclopentenyl carbinol (13a)

A mixture of 6a (1.41 g, 5.5 mmol) treithyl orthoformate (30 ml) and hydrochloric acid (12N, 140 ml) was stirred overnight. The suspension was dried in vacuo. Diluted hydrochloric acid (0.5N, 40 ml) was added and the mixture was reacted at room temperature for 1 hr. The mixture was neutralized to pH 8 with 1N sodium hydroxide and absorbed on silica gel (7.5 g) packed in a column (4.0×10 cm) and eluted by $CHCl_3$-MeOH (20:1) to yield off-white crystals of 13a, 118 g (80%). The crude product was recrystalized from ethanol to yield 13a, mp 145°-147° C. MS (30 ev, 220° C.): m/e 265 and 267 (M+ and M++2), 235 (M+-30), 169 (B+); IR: 3600-2600 ($NH_2$, OH), 1620,1580 (C=C, C=N); Anal. ($C_{11}H_{12}N_5OCl·\frac{3}{4} H_2O$) C,H,N.

EXAMPLE 22

(±)-(1α,3α)-3-(2-Amino-6-chloro-9H-purin-9-yl)-cyclopentyl carbinol (13b)

A mixture of 6b (1.3 g, 5 mmol) triethyl orthoformate (30 ml) and hydrochloric acid (12N, 1.30 ml) was stirred overnight. The reaction mixture was processed as described in Example 21 to yield off-white crystals of 13b, 1.00 g (73%), mp 151°-153° C. MS (30 ev, 230° C.): m/e 267 and 269 (M+ and M++2), 236 (M+-31), 169 (B+); IR: 3600-2600 ($NH_2$, OH), 1620,1580 (C=C, C=N); Anal. ($C_{11}H_{14}N_5OCl·\frac{1}{2} H_2O$) C,H,N.

EXAMPLE 23

(±)-(1α,4α)-4-(2-Amino-6-hydroxy-9H-purin-9-yl)-2-cyclopentenyl carbinol (14a)

A mixture of 13a (266 mg, 1 mmol) and aqueous sodium hydroxide (0.33N) was refluxed for 5 hr, absorbed onto silica gel (2 g) packed in a column (2.0×7.5 cm) and eluted with $CHCl_3$-MeOH (5:1). The crude product was recrystalized from methanol-water (1:4) to yield white crystals of 14a, 152 mg (61%), mp 254°-256° C. (dec). MS (30 ev, 200° C.): m/e 247 (M+), 127 (M+-30), 151 (B+); IR: 3600-2600 ($NH_2$, OH), 1700,1600 (C=O, C=C, C=N); Anal. ($C_{11}H_{13}N_5O_2·\frac{3}{4} H_2O$) C,H,N.

EXAMPLE 24

(±)-(1α,3α)-3-(2-Amino-6-hydroxy-9H-purin-9-yl)-cyclopentyl carbinol (14b)

Compound 13b (280 mg, 1 mmol) was hydrolyzed with sodium hydroxide and purified as described in Example 23 to yield white crystals of 14b, 204 mg (77%), mp 274°-276° C. (dec). MS (30 ev, 320° C.): m/e 249 (M+), 218 (M+-31), 151 (B+); IR: 3600-2600 ($NH_2$, OH), 1700,1600 (C=O, C=C, C=N); Anal. ($C_{11}H_{15}N_5O_2·\frac{3}{4} H_2O$) C,H,N.

EXAMPLE 25

(±)-(1α,4α)-4-(2,6-Diamino-9H-purin-9-yl)-2-cyclopentenyl carbinol (15a)

Liquid ammonia was passed into a solution of 13a (265 mg, 1 mmol) in methanol (10 ml) at −80° C. in a bomb. The bomb was sealed and heated at 75° C. for 48 hr. Ammonia and methanol were evaporated. The residue was absorbed on silica gel (2 g), packed in a column (2.0×10 cm) and eluted with $CHCl_3$-MeOH (15:1). The crude product was recrystalized from ethanol to yield 196 mg (80%) of 15a, mp 152°-155° C. MS (30 ev, 200° C.): m/e 246 (M+), 229 (M+-17), 216 (M+-30), 150 (B+); IR: 3600-3000 ($NH_2$, OH), 1700,1650,1600 (C=O, C=C, C=N); Anal. ($C_{11}H_{14}N_6O$) C,H,N.

EXAMPLE 26

(±)-(1α,3α)-3-(2,6-Diamino-9H-purin-9-yl)-cyclopentyl carbinol (15b)

Compound 13b (280 mg, 1 mmol) reacted with ammonia as described in Example 25 to yield white crystals of 15b, 193 mg (77%), mp 208°-211° C. MS (30 ev, 220° C.): m/e 248 (M+), 231 (M+-17), 217 (M+-31), 150 (B+); IR: 3600-3000 ($NH_2$, OH), 1700,1650,1600 (C=O, C=C, C=N); Anal. ($C_{11}H_{16}H_6O$) C,H, N.

EXAMPLE 27

(3S)-(1α,4α)-4-(5-Amino-7-chloro-3H-1,2,3-triazolo[4,5-d]pyrimidin-3-yl)-2-cyclopentenyl carbinol (16a)

To a cold solution of 6a (255 mg, 1 mmol) in acetic acid (1.5 ml) and water (2.5 ml) was added sodium nitrite (83 mg, 1.2 mmol) in water (2 ml). The reaction was monitored by starch-potassium iodide paper. After stirring for 1 hr at 0° C., the precipitate was filtered and washed with cold water, then dried over phosphorus pentoxide in vacuo to yield 16a as off-white crystals, 218 mg (81%). The crude 16a was recrystallized from methanol, mp 153°-155° C. (dec). MS (30 ev, 220° C.): m/e 266 and 268 (M+ and M++2), 236 (M+-30), 170

(B+); IR: 3600–3000 (NH$_2$, OH), 1650,1600 (C=C, C=N); Anal. (C$_{10}$H$_{11}$ClN$_6$O) C,H,N.

EXAMPLE 28

(±)-(1α,3α)-3-(5-Amino-7-chloro-3H-1,2,3-triazolo[4,5-d]pyrimidin-3-yl)-cyclopentyl carbinol (16)

Compound 6b (773 mg, 3 mmol) was reacted with sodium nitrite as described in Example 27 to yield 666 mg (82%) of 16b, which was recrystalized from methanol, mp 170°–172° C. (dec). MS (20 ev, 300° C.): m/e 268 and 270 (M+ and M++2), 237 (M+-31), 170 (B+); IR: 3600–3000 (NH$_2$, OH), 1650,1600 (C=C, C=N); Anal. (C$_{10}$H$_{13}$ClN$_6$O) C,H,N.

EXAMPLE 29

(±)-(1α,4α),-4-(5-Amino-7-hydroxy-3H-1,2,3-triazolo[4,5-d]pyrimidin-3-yl)-2-cyclopentenyl carbinol (17a)

A mixture of 16a (218 mg, 0.8 mmol) and aqueous sodium hydroxide (0.25N, 10 ml) was refluxed for 3 hr, then was adjusted to pH 3 with 6N hydrochloric acid. The gelatinious precipitate was filtered and washed with cold water. It was dried over phosphorous pentoxide in vacuo to yield 17a as an off-white solid, 181 mg (90%) mp 222°–224° C. (dec). After recrystalization from water, the mp was 223°–225° C. (dec). MS (20 ev, 300° C.): m/e 248 (M+), 217 (M+-31), 152 (B+); IR: 3600–3000 (NH$_2$, OH), 1750,1600 (C=C, C=N); Anal. (C$_{10}$H$_{12}$N$_6$O$_2$·½ H$_2$O) C,H,N.

EXAMPLE 30

(±)-(1α,3α)-3-(5-Amino-7-hydroxy-3H-1,2,3-triazolo[4,5-d]pyrimidin-3-yl)-cyclopentyl carbinol (17b)

Compound 16b (268 mg, 1 mmol) was hydrolyzed and processed as described in Example 29 to yield 17b as an off-white product, 203 mg (81%). The crude product was recrystalized from water to yield 17b, mp 228°–231° C. MS (20 ev, 320° C.): m/e 250 (M+), 219 (M+-31), 152 (B+); IR: 3600–3000 NH$_2$, OH), 1750,1600 (C=C, C=N); Anal. (C$_{10}$H$_{14}$N$_6$O$_2$·1.25 H$_2$O) C,H,N.

EXAMPLE 31

(±)-(1α,4α)-4-(5,7-Diamino-3H-1,2,3-triazolo[4,5-]pyrimidin-3-yl)-2-cyclopentenyl carbinol (18a)

Compound 16a (267 mg, 1 mmol) was processes as described in Example 25, employing a reaction time of 60° C. for 20 hr. The residual mixture was absorbed on silica gel (2 g), packed in a column (2.0×10 cm) and eluted by CHCl$_3$-MeOH (15:1) to yield 18a as white crystals, 204 mg (83%). The crude product was recrystalized from ethanol-water (2:1), to yield 18a of mp 240°–242° C. (dec). MS (30 ev, 240° C.): m/e 247 (M+), 229 (M+-18), 217 (M+-30), 151 (B+); IR: 3600–3100 (NH$_2$, OH), 1700,1650,1600 (C=O, C=C, C=N); Anal. (C$_{10}$H$_{13}$N$_7$O·H$_2$O) C,H,N.

EXAMPLE 32

(±)-(1α,3α)-3-(5,7-Diamino-3H-1,2,3-triazolo[4,5-d]pyrimidin-3-yl)-cyclopentyl carbinol (18b)

Compound 16b (268 mg, 1 mmol) was processed as described in Example 31 to yield 220 mg of 18b (88%) which was recrystalized from ethanol-water (1:2) to afford pink-white crystals, mp 223°–225° C. MS (30 ev, 250° C.): m/e 249 (M+), 218 (M+-31), 151 (B+); IR: 3600–3100 (NH$_2$, OH), 1700,1600 (C=C, C=N); Anal. (C$_{10}$H$_{15}$N$_7$O) C,H, N.

EXAMPLE 33

(±)-(1α,4α)-4-(3-Methoxy-2-methylacryloylureido)-2-cyclopentenyl carbinol (19a)

Isocyanate reagent was prepared from 3-methoxy-2-methylacryloyl chloride (1.00 g, bp 65°–66° C./2.5 mm) in anhydrous benzene (10 ml) and freshly dried silver cyanate (2.6 g, 17 mmol, dried at 110° C., 2 hr) by refluxing for 0.5 hr. The supernatant was added dropwise into a solution of 2a (from 1a, 0.8 g, 4 mmol) in N,N-dimethylformamide (10 ml) at −15° C. and the mixture was stirred for 1 hr, then stored at 4° C. overnight. The solvent was evaporated and the residue was absorbed on silica gel (3 g), packed in a column (2.0×16 cm) and eluted with CHCl$_3$-MeOH (20:1) to yield white crystals of 19a, 605 mg, (60%), mp 147°–149° C. MS (30 ev, 200° C.): m/e 254 (M+), 239 (M+-15), 223 (M+-31), 158 (B+); IR: 3600–2800 (NH$_2$, OH), 1700,1650,1600 (C=O, C=C); Anal. (C$_{12}$H$_{18}$N$_2$O$_4$) C,H,N.

EXAMPLE 34

(±)-(1α,4α)-4-[5-Methyl-2,4-(1H,3H)-pyrimidinedion-3-yl]-2-cyclopentenyl carbinol (20a)

A mixture of 19a (381 mg, 1.5 mmol), p-toluenesulfonic acid monohydrate (20 mg) and anhydrous N,N-dimethylformamide (2 ml) was stirred at 115° C. for 3 hr. The solvent was evaporated, the residue was absorbed on silica gel (3 g), packed in a column (2.0×14 cm) and eluted with CHCl$_3$-MeOH (20:1) to yield 20a as off-white crystals, 206 mg (62%). The product was recrystalized from absolute ethanol to yield 20a, mp 213°–215° C. MS (30 ev, 250° C.): m/e 222 (M+), 204 (M+-18), 191 (M+-31), 126 (B+); IR: 3600–3300 (OH), 1700,1600 (C=O, C=C); Anal. (C$_{11}$H$_{14}$N$_2$O$_3$) C,H,N.

EXAMPLE 35

Cytotoxicity Assay

The ED$_{50}$ cytotoxicity concentration determined for analogs 16a, 16b, 17a and 17b in the P-388 mouse leukemia cell culture assay are given in Table II.

TABLE II

| Inhibitory Concentrations of Carbocyclic Nucleosides for P-388 Leukemia Cells in Cultures* | |
|---|---|
| Compound | ED$_{50}$, mg/ml |
| 16a | 1.0 |
| 16b | 12.5 |
| 17a | 4.5 |
| 17b | 50.0 |

*Assay Technique: R. G. Almquist and R. Vince. J. Med. Chem., 16, 1396 (1973).

EXAMPLE 36

Anti-HIV Assay

Compound 14a was screened for anti-HIV activity at the National Cancer Institute, Frederick Cancer Research Facility, Frederick, Md. (FCRF). The following are the current screening mode operational procedures utilized at FCRF. The protocol consists of 3 areas, (I) preparation of infected cells and distribution to the test plates, (II) preparation of drug dilution plates and distribution to the test plates, and (III) XTT assay procedure. See D. A. Scudiero et al., "A New Simplified Tetrazolium Assay for Cell Growth and Drug Sensitivity in Culture," Cancer Res., 48,4827 (1988).

I. Infection and Distribvution of ATH8 Cells to Microtiter Trays

The AYTH8 cells (a normal lymphoblastoid cell line which expresses CD4) are placed in 50 ml conical centrifuge tubes and treated for 1 hr with 1–2 μg/ml of polybrene at 37° C. The cells are then pelleted for 8 min. at 1200 RPM. HIV virus, diluted 1:10 in media (RMP1-1640, 10% human serum or 15% fetal calf serum (FSC), with IL-2 and antibiotics) is added to provide an MOI of 0.001. Medium alone is added to virus-free control cells. Assuming an infectious virus titer of $10^{-4}$, an MOI of 0.001 represents 8 infectious virus particles per 10,000 cells. About 500,000 cells/tube are exposed to 400 μl of the virus dilution. The resultant mixture is incubated for 1 hr at 37° C. in Air-$CO_2$. The infected or uninfected cells are diluted to give $1 \times 10^{-4}$ (with human serum or $2 \times 10^{-4}$ (with fetal calf serum) cells/100 μl.

Infected or uninfected cells (100 μl) are distributed to appropriate wells of a 96 well, U-bottom, microtiter plate. Each compound dilution is tested in duplicate with infected cells. Uninfected cells are examined for drug sensitivity in a single well for each dilution of compound. Drug-free control cells, infected and unifected, are run in triplicate. Wells B2 through G2 served as reagent controls and received medium only. The plates are incubated at 37° C. in Air-$CO_2$ until the drug is added.

II. Drug Dilution and Addition

Dilution plates (flat bottom 96 well, microtiter plates) are treated overnight with phosphate buffered saline (PBS) or media containing at least 1% FCS or 1% human serum (depending on the medium used in the test), beginning the day before assay. This "blocking" procedure is used to limit the absorption of drug to the mcirotiter tray during the dilution process. The wells are filled completely with the blocking solution and allowed to stand at room temperature in a humidified chamber in a hood.

The dilution process is begun by first diluting the test compound 1:20. Blocked, dilution plates are prepared by flicking out the blocking solution and blotting dry on sterile gauze. All wells of each plate are then filled with 225 μl of the appropriate medium using a Cetus liquid handling system. Twenty-five microliters (25 μl) of each 1:20 diluted compound is then manually added to row A of a blocked and filled dilution plate. Four compounds, sufficient to supply two test plates, are added per dilution plate. The four compounds are then serially diluted 10 fold from row A through row H using the Cetus liquid handling system. The starting dilution of each compound in row A is, at this point, 1:200. The dilution plates are kept on ice until needed.

Using a multi-channel pipettor with 6 microtips, 100 μl of each drug dilution is transferred to the test plate which already contains 100 μl of medium plus cells. The final dilution, in the test plate, starts at 1:400 (wells B4 through G4). This dilution (to 0.25% DMSO) prevents the DMSO vehicle from interfering with cell growth. Drug-free, infected or uninfected cells (wells B3 through G3) and reagent controls (B2 through G2) receive medium alone. The final 2 compounds are then transferred from wells H7 through H12 to a second test plate using the same procedure. Test plates are incubated at 37° C. in Air-$CO_2$ for 7–14 days or until virus controls are lysed as determined macroscopically.

III. Quantitation of Viral Cytopathogenicity and Drug Activity

A. Materials

1. A solution of 2,3-bis[2-methoxy-4-nitro-5-sulfophenyl]-5-[(phenylamino) carbonyl]-2-H-tetrazolium hydroxide. (XTT) - 1 mg/ml sulution in media without FCS. Store at 4° C. Prepare weekly.

2. Phenazine methosulfonate (PMS) stock solution - This Can be prepared and maintained frozen until needed at −20° C. It should be made in PBS to a concentration of 15.3 mg/ml.

B. Microculture Tetrazolium Assay (MTA)

1. Preparation of XTT-PMS Solution - The XTT-PMS is prepared immediately prior to its addition to the wells of the culture dish. The stock PMS solution is diluted 1:100 (0.153 mg/ml). Diluted PMS is added to every ml of XTT required to give a final PMS concentration of 0.02 mM. A 50 μl aliquot of the XTT-PMS mixture is added to each of the appropriate wells, and the plate is incubated for four hours at 37° C. The plate lids are removed and replaced with adhesive plate sealers (Dynatech cat 001-010-3501). The sealed plate is shaken on a microculture plate mixer and the absorbance is determined at 450 nm.

IV. Results

Figure 2:
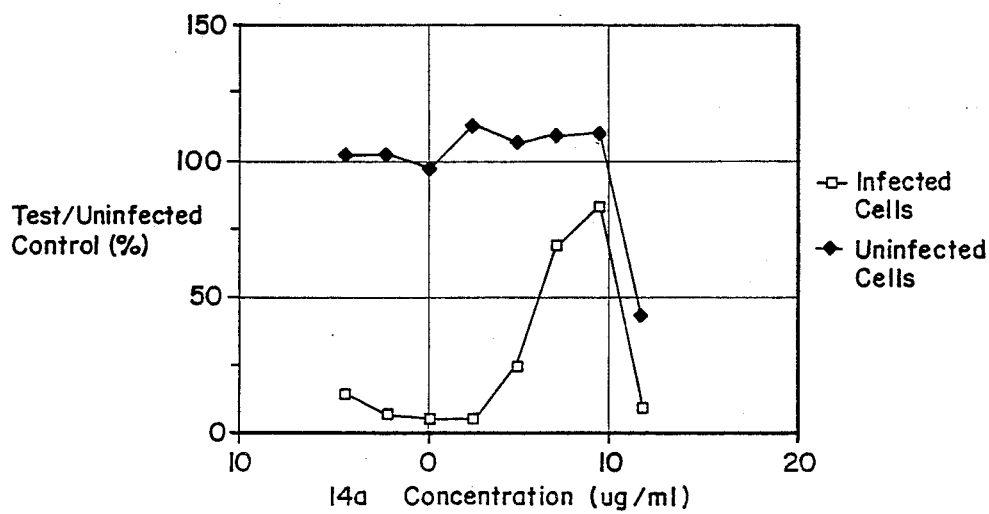
FIG. 2 is a graphic depiction of cells exposed to 14a/control cells (%) plotted vs. concentration of 14a for both uninfected cells and cells infected with HIV.

FIG. 2 depicts a plot of the percentage of test cells over uninfected cells (%) for both infected and uninfected cells as a function of the increasing concentration of compound 14a.

The data plotted on FIG. 2 permit the calculation of an effective concentration ($EC_{50}$) with respect to infected cells of about 0.15 μg/ml, an inhibitory concentration ($IC_{50}$) with respect to normal cells of about 100 μg/ml, and a therapeuitc index ($TI_{50}$) of about 667. An earlier assay carried out at the Southern Research Institute yielded at $TI_{50}$ of about 200 when MT-2 cells were cultured with H9/HTLV-IIIB.

The invention comprises the biologically active compounds as disclosed or the pharmaceutically acceptable salts or esters thereof, together with a pharmaceutically acceptable carrier for administration in effective nontoxic dose form. Pharmaceutically acceptable salts may be salts of organic acids, such as acetic, lactic, malic or p-toluene sulphonic acid and the like as well as salts of pharmaceutically acceptable mineral acids, such as hydrochloric or sulfuric acid and the like. Other salts may be prepared and then converted by conventional double decomposition methods into pharmaceutically acceptable salts directly suitable for purposes of treatment of viral infections in mammals or for the prevention of viral contamination of physiological fluids such as blood or semen in vitro.

The compounds of the general formula I or II may exist in the form of optical isomers, and these isomers, as well as racemic (±) mixtures are included within the compounds of this invention.

Pharmaceuticaloly acceptable carriers are materials useful for the purpose of administering the present analogs and may be solid, liquid or gaseous materials, which are otherwise inert and medically acceptable and are compatible with the active ingredients. Thus, the present active compounds can be combined with the carrier and added to physiological fluids in vitro or administered in vivo parenterally, orally, used as a suppository or pessary, applied topically as an ointment, cream, acrosol, powder, or given as eye or nose drops, etc., depending upon whether the prepartion is used for treatment of internal or external viral infections.

For internal virus infections, the compositions may be administered orally or parenterally at effective non-toxic antivirus dose levels of about 10 to 750 mg/kg/day of body weight given in one dose or several smaller doses throughout the day. For oral administration, fine powders or granules may contain diluting, dispersing and/or surface active agents and may be presented in water or in a syrup; in capsules in the dry state, or in a non-aqueous solution or suspension; in tablets or the like. Where desirable or necessary, flavoring, preserving, suspending, thickening or emulsifying agents may be included. For parenteral administration, administration as drops, the compounds may be presented in aqueous solution in an effective non-toxic dose in concentration of from about 0.1 to 10 percent w/v. The solutions may contain antoxidants, buffers and the like. Alternatively, for infections of external tissues, the compositions are preferably applied as a topical ointment or cream in concentration of about 0.1 to 10 percent w/v.

The invention has been described with reference to varius specific and preferred embodiments and techniques. However, it should be understood that many variations and modifications may be made while remaining within the spirit and scope of the invention.

What is claimed is:

1. A compound of the formula:

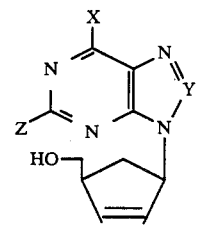

wherein X is OH NH$_2$ or Cl, Z is NH$_2$ and Y is CH or N, and the pharmaceutically acceptable salts thereof.

2. The compound of claim 1 wherein X is Cl.
3. The compound of claim 1 wherein X is OH.
4. The compound of claim 1 wherein X is NH$_2$.
5. A compound of the formula:

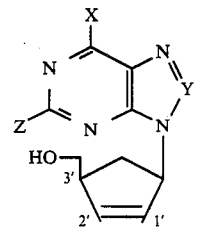

wherein Z is H, OH or NH$_2$, Y is CH or N, and X is selected from the group consisting of H, N(R)$_2$, SR, OR and halogen, wherein R is H, lower(C$_1$-C$_4$)alkyl, aryl or mixtures thereof, and the pharmaceutically-acceptable salts thereof.

6. The compound of claim 5 wherein Y is CH.
7. The compound of claim 6 wherein Z is H.
8. The compound of claim 7 wherein X is Cl.
9. The compound of claim 7 wherein X is NH$_2$.
10. The compound of claim 7 wherein X is SH.
11. The compound of claim 6 wherein Z is NH$_2$.
12. The compound of claim 11 wherein X is Cl.
13. The compound of claim 11 wherein X is OH.
14. The compound of claim 11 wherein X is NH$_2$.

* * * * *

UNITED STATES PATENT AND TRADEMARK OFFICE
CERTIFICATE OF CORRECTION

PATENT NO. : 4,916,224
DATED      : April 10, 1990
INVENTOR(S) : Vince, et al.

It is certified that error appears in the above-identified patent and that said Letters Patent is hereby corrected as shown below:

At col. 10, line 65, "(269%)" should read --(69%)--.

At col. 11, line 41, "treithyl" should read --triethyl--.

At col. 12, line 12, "127" should read --217--.

At col. 12, lines 56-57, "(35)" should read --(±)--.

At col. 13, lines 46-47 "[4,5-]" should read --[4,5-d]--.

At col. 15, line 6, for "AYTH8" should read --ATH8--.

At col. 15, line 12, for "(FSC)" should read --(FCS)--.

Signed and Sealed this

Twenty-sixth Day of November, 1991

Attest:

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,916,224

DATED : April 10, 1990

INVENTOR(S) : Vince, et al.

It is certified that error appears in the above-identified patent and that said Letters Patent is hereby corrected as shown below:

At col. 3, lines 25-46, for " 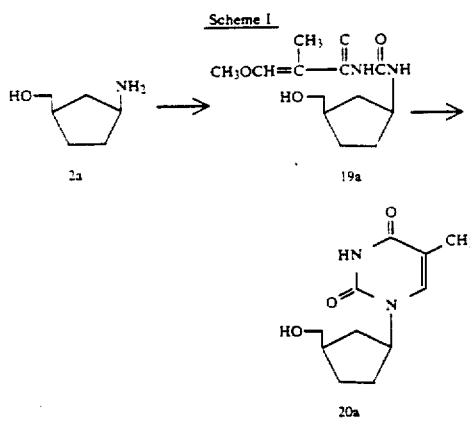 " read -- 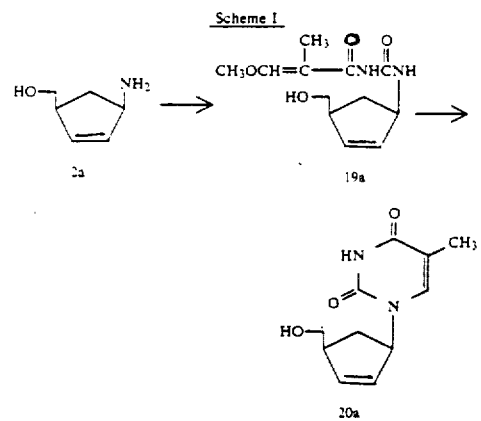 --

At col. 4, line 62, for "3α" read --4α--.

Signed and Sealed this

Twenty-ninth Day of December, 1992

Attest:

DOUGLAS B. COMER

Attesting Officer     Acting Commissioner of Patents and Trademarks